United States Patent [19]

DeVringer et al.

[11] Patent Number: 5,690,923

[45] Date of Patent: Nov. 25, 1997

[54] STABLE TOPICAL RETINOID COMPOSITIONS

[75] Inventors: Tom DeVringer, Zoetermeer; Antoon Van Harrewijn, Delft; Aart Muehlenbruch, Haarlem, all of Netherlands

[73] Assignee: Yamanouchi Europe B.V., Leiderdorp, Netherlands

[21] Appl. No.: 571,898

[22] PCT Filed: Jul. 1, 1994

[86] PCT No.: PCT/NL94/00151

§ 371 Date: Dec. 28, 1995

§ 102(e) Date: Dec. 28, 1995

[87] PCT Pub. No.: WO95/01160

PCT Pub. Date: Jan. 12, 1995

[30] Foreign Application Priority Data

Jan. 7, 1993 [EP] European Pat. Off. ............ 93201931

[51] Int. Cl.[6] .................................................. A61K 31/74
[52] U.S. Cl. ................................ 424/78.02; 424/78.03; 514/725
[58] Field of Search ................. 514/725; 424/78.02, 424/78.03

[56] References Cited

U.S. PATENT DOCUMENTS

| 4,532,133 | 7/1985 | Schmidt | 514/725 |
|---|---|---|---|
| 5,043,356 | 8/1991 | Fulton, Jr. | 514/549 |

FOREIGN PATENT DOCUMENTS

| 0393904 | 10/1990 | European Pat. Off. . |
|---|---|---|
| 0481725 | 4/1992 | European Pat. Off. . |
| 9014833 | 12/1990 | WIPO . |

*Primary Examiner*—Terressa Mosley
*Attorney, Agent, or Firm*—McDonnell Boehnen Hulbert & Berghoff

[57] ABSTRACT

Compositions for topical application to the skin are provided, which compositions comprise a retinoid in an aqueous vehicle, and further contain at least one non-ionic surfactant, wherein the non-ionic surfactant is the crystallization-preventing and stabilizing agent for said retinoid and is selected from the group consisting of polyoxyethylene mono fatty alcohol ethers, polyoxyethylene glyceryl fatty acid triesters and ethyleneoxide/propyleneoxide block copolymers.

8 Claims, No Drawings

STABLE TOPICAL RETINOID COMPOSITIONS

The present invention relates to aqueous pharmaceutical and cosmetic compositions, comprising a retinoid, for topical application to the skin.

BACKGROUND OF THE INVENTION

Topical compositions, comprising a retinoid in an aqueous vehicle, are known.

Vitamin A acid or retinoic acid, IUPAC name 3,7-dimethyl-9-(2,6,6-trimethyl-1-cyclohexen-1-yl)-2,4,6,8-nonatetraenoic acid, has been used topically for the treatment of acne vulgaris and recently also for the treatment of ageing skin. The naturally occurring form is the all-trans compound or tretinoin, but cis compounds are also known. The 13-cis compound or isotretinoin is also used as a keratolytic agent. Both isomers and derivatives thereof, such as salts, esters and amides, and structural analogues, such as etretinate, belong to the group of the retinoids.

WO 90/14833 (Bazzano) discloses a stable, aqueous composition for topical application to the skin, comprising a retinoid. Said composition may also comprise 0.1 to 20 wt % of a solubilising agent (ethanol) and a surfactant, the last mentioned ingredient being added in order to have the dual benefit of helping to maintain the active ingredient in uniform suspension in the formulation, while enhancing the bioavailability of the active ingredient.

However, the stability of the compositions is still rather limited: table II at page 17 mentions the percentage decomposition of tretinoin in 7 formulations, said percentage ranging from 3 to 13% after 10 months' storage. Furthermore, all examples show compositions comprising a substantial amount of the solubilising agent ethanol. It, thus, is to be expected that said compositions, due to the presence of said solubilising agent, still cause irritation and inflammation of the skin.

EP-A-393904 (Maxam) discloses a water-based, alcohol-, oil- and fat-free formulation comprising tretinoin in a not completely solvated form, a gelling agent and a proteinaceous material for stabilising the gelling agent. The formulation may further comprise one or more of an antioxidant, a preservative and glycerin. A surfactant, the choice of which does not seem to be critical, may also be incorporated in the formulation to allow good dispersion of the active ingredient and to enhance skin penetration. The compositions are said to be physically and chemically stable. However, it is well-known that proteinaceous materials, such as proteins, polypeptides, peptides, amino acids and mucopolysaccharides as mentioned in the specification, are prone to microbial attack and/or chemical degradation, especially in aqueous vehicles. Therefore, the stabilising effect exerted by said materials will be limited.

Reference is made further to U.S. Pat. Nos. 4,022,913 and 4,532,133 which both disclose compositions comprising vitamin-A alcohol esters for uses like high potency vitamin preparations and additives in animal feed.

The compositions of the present invention comprise compounds derived from vitamin-A acid which are not the subject of above references.

Retinoids are insoluble or at most very slightly soluble in water, but readily soluble in e.g. ethanol. Therefore retinoid containing preparations have been most effectively applied using an alcohol containing solvent system, which causes an uncomfortable burning sensation by itself. Said sensation is amplified when applied to skin which was previously or is simultaneously treated with retinoic acid. Cream formulations were found to be generally more acceptable to patients, but they were found to have other disadvantages, such as a reduced clinical effectiveness as compared with alcoholic compositions containing the same amount of retinoic acid and sometimes a comedogenic effect due to fats and oils, used in the formulations. Aqueous retinoic acid preparations containing no alcohol and no fats have not shown to be clinically very effective, due to the fact that the active ingredient is not dissolved and, thus, not available for exerting the desired effect.

There, thus, exists a need for a composition comprising a retinoid, which composition:

is chemically and physically stable;

does not contain alcohol; and is clinically at least as effective as a prior art composition, containing said retinoid in an alcoholic vehicle.

SUMMARY OF THE INVENTION

The present invention provides a composition, comprising a retinoid in an aqueous vehicle, containing at least one crystallisation preventing and stabilising agent, chosen from the group of non-ionic surfactants. It is another object of the present invention to provide a method for the preparation of aqueous compositions comprising a retinoid by the use of at least one crystallisation preventing and stabilising agent; said agent being chosen from the group of non-ionic surfactants.

DETAILED DESCRIPTION OF THE INVENTION

Non-ionic surfactants are known per sé and expendiently the composition according to the invention comprises a non-ionic surfactant chosen from a polyoxyalkylene compound, a polyoxyalkylene polymer, a polyoxyalkylene block copolymer or a mixture of two or more of such substances. Generally the alkylene moiety of said substances comprises from 2 to 5 carbon atoms, preferably 3 or 4 carbon atoms. In particular above non-ionic surfactants are represented by polyoxyethylene fatty alcohol ethers, polyoxyethylene glyceryl fatty acid triesters and ethylene oxyde-propylene oxyde block copolymers.

Very suitable representatives of above non-ionic surfactants are polyoxyethylene (4) monolaurylether, polyoxyethylene (25) glycerintrioleate and a liquid ethyleneoxyde / propylene-oxyde block copolymer containing 40% of ethylene oxyde and 60% of propylene oxyde and having a molecular weight of 2.000–3.000 (SYNPERONIC PE/L44®) respectively.

In a further advantageous embodiment a composition according to the invention comprises a further non-ionic surfactant chosen from the group of polyoxyethylene glycerin fatty acid monoesters such as polyoxyethylene (15) glycerin monolaurate.

It has been found that the addition of at least one crystallisation preventing and stabilising agent to compositions comprising a retinoid in an aqueous vehicle having a pH of between 3 and 7, surprisingly leads to an improvement of the chemical stability of the active ingredient. This has in particular been demonstrated for compositions, comprising a retinoid and a polyoxyethylene monoether in an aqueous vehicle, both upon storage at elevated temperatures during several months and upon storage at ambient conditions during at least 18 months.

On microscopic evaluation of the compositions according to the invention no crystals of the active ingredient have been observed, also not after storage for more than one year at room temperature. In order to increase the availability of the active ingredient and, thus, its clinical efficacy, an organic solvent, such as a monohydric $C_1$–$C_3$-alkanol and especially ethanol and/or isopropylalcohol, had to be incorporated in prior art compositions comprising retinoic acid. In the compositions according to the present invention no substantial amounts of such organic solvent are needed, although it may be present in an amount of up to 5 wt %, preferably up to 1 wt % and more preferably in an amount of 0–0.1 wt %. An advantage of the compositions according to the present invention is that the extreme drying effect on the skin, due to the use of relatively high amounts of organic solvents in prior art compositions, has been avoided. Furthermore, water-based compositions do not provide any problem relating to environmental and safety aspects.

The compositions according to the present invention comprise a topically effective amount of a retinoid and can be successfully used for the topical treatment of acne vulgaris and of ageing skin. However, other topically effective drugs, which may enhance the therapeutic effect of the retinoid, may be incorporated without any negative effect on the stability or clinical efficacy. Examples thereof are corticosteroids and antibiotics. Preferably, water soluble antibiotics such as clindamycin phosphate or the hydrochloric acid addition salt thereof are used. The combination products of retinoic acid and clindamycin phosphate according to the invention have proved to be in particular suitable for the mixed forms of acne vulgaris: comedonic acne with mild to moderate inflammation. For this indication usually either a topical antibiotic-containing preparation or a topical tretinoin-containing preparation is prescribed. Once daily application of the combination products according to the invention suffices.

The concentration of a retinoid in the composition may range from 0.001 to 0.5 wt %, preferably from 0.01 to 0.1 wt % and most preferably from 0.025 to 0.05 wt %.

As indicated earlier an advantageous group of non-ionic surfactants is formed by the polyoxyethylene monoethers such as polyoxyethylene (4) monolauryl ether. The latter product is also known under the CTFA-name Laureth-4 and available on the market under the Trade Names BRIJ 30; VOLPO L4 and SIMULSOL P4 .

A further advantageous group of non-ionic surfactants is constituted by the polyoxyethylene glyceryl fatty acid tri esters such as polyoxyethylene (25) glyceryltrioleate. The latter product is on the market available under the trade name TAGAT TO.

Another advantageous group of non-ionic surfactants is formed by the ethylene oxyde / propyleneoxyde block copolymers; an example of the latter product is SYNPERONIC PE/L44.

Above products give, when incorporated in a composition according to the invention, good results in terms of stability and applicability.

Further improvements are found when in addition to the non-ionic surfactants referred to a product chosen from the group of polyoxyethylene glycerin fatty acid monoesters is included. A typical representative thereof is polyoxyethylene (15) glycerin monolaurate which is available under the trade name Glycerox L15®.

The amount of the non-ionic surfactants to be added to the compositions depends on the amount and on the type of active ingredient(s) used, but in general ranges from 0.5 to 20 wt %, preferably from 1 to 10 wt % and more preferably from 2–5 wt %. If a combination of polyoxyethylene monoether and a polyoxyethylene glycerin monoester is used the molecular ratio of these compounds is between 10:1 and 1:1 (polyoxyethylene monoether:polyoxyethylene-glycerin monoester) and, if the combination of laureth-4 and polyoxyethylene-(15)-glycerol monolaurate is selected, preferably about 2.5. However, it is also possible to use a mixture of representatives from each group of non-ionics.

The viscosity of the aqueous vehicle may be increased by the addition of viscosity enhancers well-known in the art, viz. cellulose-derivatives, such as hydroxypropyl cellulose, and polyacrylic acids, such as those available under the registered trademark Carbopol.

The pH of the compositions is preferably adjusted by the addition of a physiologically acceptable buffering agent to a pH of between 3 and 7, but preferably of between 4.0 and 5.5.

As the retinoid is susceptible to oxidation and resulting decomposition in an aqueous medium, the compositions of the present invention optionally also contain an effective amount of one or more anti-oxidants in a suitable concentration relative to the active ingredient, such as from about 0.01 to 4% by weight of the composition. Due to the above-mentioned combination of surfactants, the effective concentration of the anti-oxidant(s) in the compositions of the present invention may be reduced as compared to prior art compositions comprising retinoic acid.

The compositions may contain up to about 10% of an emollient or anti-irritant as an additional help in relieving any drying effects on the skin which is an intrinsic property of the active ingredient. Examples of said emollients are $C_{12}$–$C_{22}$ fatty alcohols and fatty acid esters, silicone oils and vegetable oils. Examples of anti-irritants are natural moisturizing factor, humectants, etc..

The compositions of the present invention may further comprise other appropriate excipients, such as sequestrants, buffers and preservatives.

The compositions are preferably prepared according to methods as known in the art for the preparation of compositions comprising compounds which may be readily oxidized in the presence of light and/or oxygen. Due to the above-mentioned combination of surfactants the total exclusion of oxygen during the preparation of the compositions of the present invention may not be required.

In a clinical pilot study an aqueous composition according to the present invention has proved to be at least as effective as a commercially available prior art composition, comprising retinoic acid in an alcoholic vehicle.

All publications and patent applications cited in this specification are herein incorporated by reference as if each publication or patent application were specifically and individually indicated to be incorporated by reference.

Although the foregoing invention has been described in some detail by way of illustration and example for purposes of clarity and understanding, it will be readily apparent to those of ordinary skill in the art in the light of the teachings of this invention that certain changes and modifications may be made thereto without departing from the spirit and scope of the appended claims.

The following examples will illustrate the invention; all percentages are in weight unless otherwise indicated.

EXAMPLES

Example 1

| | |
|---|---|
| retinoic acid | 0.025% |
| disodium edetate | 0.10% |
| butylhydroxytoluene | 0.02% |
| CARBOPOL ® 980 | 1.0% |
| laureth-4 | 2.0% |
| tromethamine | 0.75% |
| citric acid monohydrate | 0.15% |
| propyleneglycol | 7.5% |
| methylhydroxybenzoate | 0.1% |
| water till | 100.0% |

I. Carbopol was added to a mixture of propyleneglycol and water.

II. Laureth-4 was heated until 35°–40° C., whereafter butyl-hydroxytoluene, retinoic acid and methylhydroxybenzoate were added. The mixture was stirred until complete dissolution of the components was achieved, excluding oxygen, protected against the influence of light.

III. Citric acid monohydrate and tromethamine were dissolved in water under stirring and heating until 50°–60° C.

Whilst stirring phase II was first added to phase I, and thereafter phase III was added, protected against light at a temperature of 50°–60° C. The whole was put under vacuum, stirred, further put under vacuum and subsequently cooled till the temperature dropped below 30° C. Nitrogen was added and the product was removed from the ointment mixer.

Example 2

| | |
|---|---|
| retinoic acid | 0.025% |
| clindamycin phosphate | 1.20% |
| disodium edetate | 0.10% |
| butylhydroxytoluene | 0.02% |
| CARBOPOL ® 980 | 1.0% |
| laureth-4 | 4.0% |
| tromethamine | 0.75% |
| citric acid monohydrate | 0.15% |
| propyleneglycol | 7.5% |
| methylhydroxybenzoate | 0.1% |
| water till | 100.0% |

The gel was prepared according to the manufacturing method of example 1; clindamycin phosphate was dissolved in water together with citric acid monohydrate and tromethamine.

Example 3

Example 2 was repeated but now instead of 4% Laureth 4 a mixture of 2% Laureth 4 (polyoxyethylene (4) monolauryl-ether) and 2% GLYCEROX L15 (polyoxyethylene (15) glycerinmono-laurate) was used.

An equally good product, in terms of stability and applicability, was obtained.

Example 4

Example2 was repeated but instead of 4% Laureth-4 4% of either SYNPERONIC PE/L44 or TAGAT TO was used.

An equally good product, in terms of stability and applicability, was obtained.

Example 5

A double-blind, randomized, multi-center pilot study in 40 patients with moderate to severe acne vulgaris, grade 3 or higher on the scoring scale of Cook was performed in order to compare the efficacy of a prior art composition, comprising 0.025 wt % retinoic acid in an alcoholic gel vehicle, and a composition according to the present invention (the aqueous gel of example 2).

The medication was applied once daily at night on the acne lesions for a period of 12 weeks.

Both treatment groups responded to the therapy. The patients treated with the composition of example 2 had a more rapid response and the number of inflamed lesions after 12 weeks was significantly lower than the patients treated with the alcoholic retinoic acid gel. The treatment groups showed to be comparable with respect to the non-inflamed lesions, although a numerical difference in favour of the composition according to the present invention could be assessed.

We claim:

1. A composition for topical application to the skin comprising a retinoid in an aqueous vehicle said aqueous vehicle further comprising up to 5 wt % of an organic solvent, and at least one non-ionic surfactant wherein the aqueous vehicle has a pH of between 3 and 7 and the non-ionic surfactant is a crystallization preventing and stabilizing agent for said retinoid and is selected from the group consisting of a) polyoxyethylene mono fatty alcohol ethers, b) polyoxyethylene glyceryl fatty acid triesters, and c) ethylene oxide/proclaim oxide block copolymers.

2. A composition according to claim 1 wherein the non-ionic surfactant is selected from the group consisting of a) polyoxyethylene (4) monolaurylether, b) polyoxyethylene (25) glyceryltrioleate, and c) SYNPERONIC PE/L44, a liquid ethyleneoxide/propyleneoxide block copolymer containing 40% of ethyleneoxide and 60% of propyleneoxide and having a molecular weight of 2.000–3.000 respectively.

3. A composition according to claim 1 comprising a further non-ionic surfactant chosen from the group of polyoxyethylene glycerin fatty acid monoesters.

4. Composition according to claim 4 wherein the polyoxyethylene glycerin fatty acid monoester is polyoxyethylene (15) glycerin monolaurate.

5. A composition according to claim 1 wherein 0–0.1 wt % of the organic solvent is present.

6. Composition according to claim 5, wherein the organic solvent is a monohydric $C_1$–$C_3$ alkanol.

7. A composition according to claim 1 wherein the composition contains an antibiotic.

8. Composition according to claim 7 wherein the antibiotic is clindamycin or a derivative thereof.

* * * * *